(12) United States Patent
Amer et al.

(10) Patent No.: US 11,708,552 B2
(45) Date of Patent: Jul. 25, 2023

(54) MULTI-CHAMBER BIOREACTOR APPARATUS

(71) Applicant: The Board of Regents for Oklahoma State University, Stillwater, OK (US)

(72) Inventors: Momen Mohsen Ahmed Amer, Stillwater, OK (US); Joshua D. Ramsey, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 617 days.

(21) Appl. No.: 16/603,006

(22) PCT Filed: Apr. 11, 2018

(86) PCT No.: PCT/US2018/027150
§ 371 (c)(1),
(2) Date: Oct. 4, 2019

(87) PCT Pub. No.: WO2018/191405
PCT Pub. Date: Oct. 18, 2018

(65) Prior Publication Data
US 2020/0032185 A1    Jan. 30, 2020

Related U.S. Application Data

(60) Provisional application No. 62/484,194, filed on Apr. 11, 2017.

(51) Int. Cl.
| | | |
|---|---|---|
| *C12M 1/00* | (2006.01) | |
| *C12M 3/00* | (2006.01) | |
| *C12M 1/06* | (2006.01) | |
| *C12M 1/34* | (2006.01) | |
| *C12M 1/02* | (2006.01) | |

(52) U.S. Cl.
CPC ............ *C12M 23/14* (2013.01); *C12M 23/26* (2013.01); *C12M 23/48* (2013.01); *C12M 27/02* (2013.01); *C12M 41/00* (2013.01); *C12M 41/12* (2013.01)

(58) Field of Classification Search
CPC ........ C12M 1/00; C12M 23/14; C12M 23/26; C12M 23/48; C12M 23/58; C12M 27/02; C12M 3/00; C12M 41/00; C12M 41/12; C12M 41/48
See application file for complete search history.

(56) References Cited

U.S. PATENT DOCUMENTS

2015/0368602 A1* 12/2015 Galliher ................. C12M 29/00
435/293.1
2017/0073624 A1* 3/2017 Stankowski ........... C12M 23/34

* cited by examiner

*Primary Examiner* — Lydia Edwards
(74) *Attorney, Agent, or Firm* — Dunlap Codding, P.C.

(57) ABSTRACT

A multi-chamber single-use bioreactor for cell culture expansion has bag assembly and a rigid support structure defining a bag receiving space. The bag assembly disposed in the bag receiving space of the rigid support structure and supported by the rigid support structure. The bag assembly has at least a first flexible bag and a second flexible bag. The first bag defines a first reaction chamber, and the second bag defines a second reaction chamber. The first reaction chamber has a first volume, a first inlet, and a first outlet, and the second reaction chamber has a second volume different from the first volume, a second inlet, and a second outlet. The second inlet of the second bag is fluidically connected to the first outlet of the first bag so liquid in first reaction chamber can be transferred to the second reaction chamber.

8 Claims, 2 Drawing Sheets

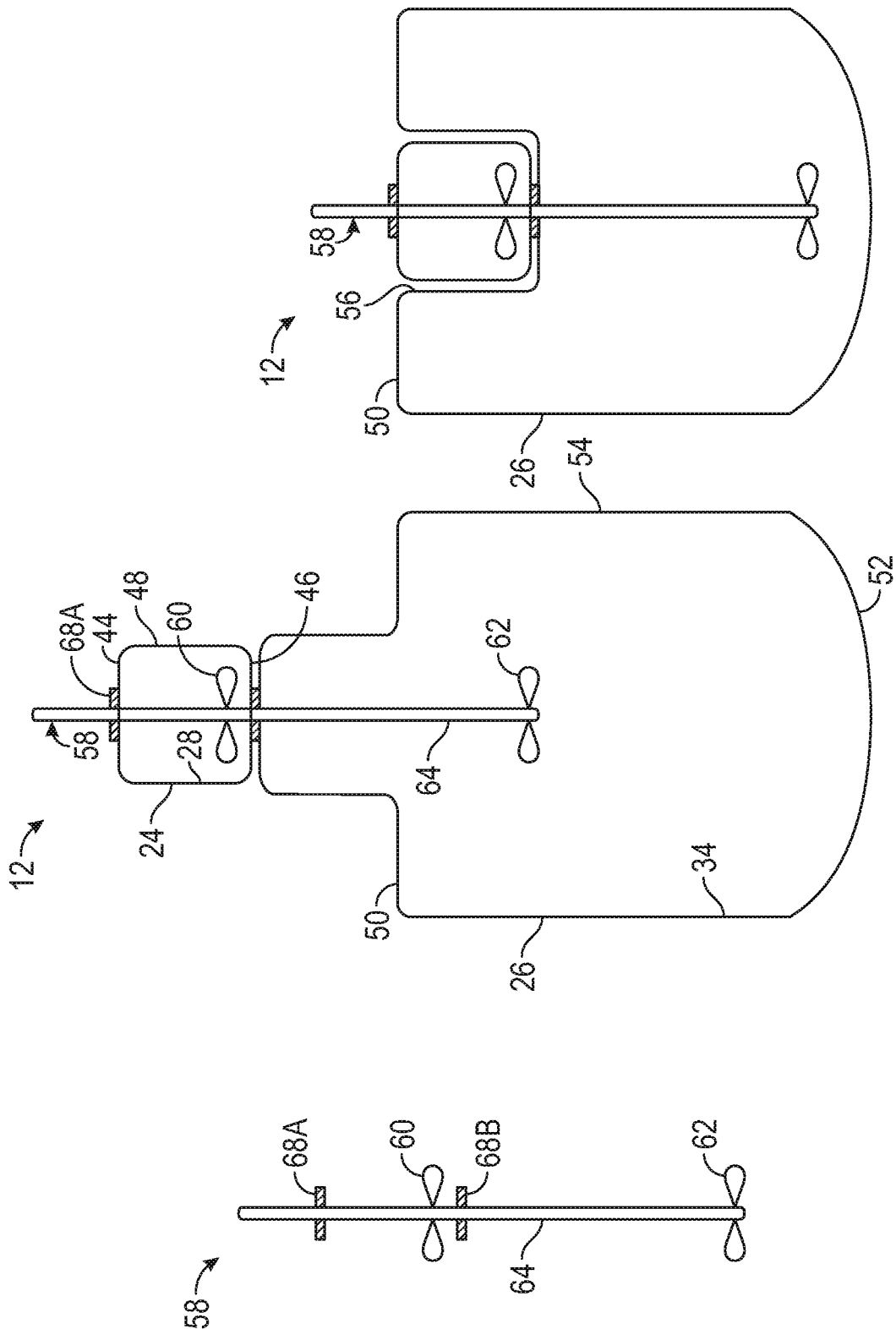

MULTI-CHAMBER BIOREACTOR APPARATUS

CROSS REFERENCE TO RELATED APPLICATIONS

This application claims the benefit of U.S. Provisional Patent Application Ser. No. 62/484,194, filed on Apr. 11, 2017, the entire contents of which being hereby expressly incorporated herein by reference.

BACKGROUND

Stainless steel bioreactors have been the gold standard in biopharmaceutical industry for years. However, several disadvantages for using such conventional bioreactors have been identified including the on-going need for re-sterilization, the time required to clean them between batches, and the increased risk of cross contamination either between different cell lines or between different proteins produced in the same bioreactor. These drawbacks have led to the evolution of single use bioreactors, which have seen increased use over the past few years.

Single use bioreactors are plastic bags that are pre-sterilized by their suppliers, usually by gamma irradiation, and sterilization and cleaning are not required. This eliminates the need of large space and costs of cleaning in place (CIP) and sterilization in place (SIP) installations and eliminates the need for establishing a cleaning validation procedure. Also, these single use systems reduce risks of cross contamination and production turnaround times as they allow companies to shift between target proteins and cell lines in the production process quickly and inexpensively. These advantages of single use technology shorten the time required for product launch to the market. Benefits of flexible bag containers include faster facility set-up, reduction of down time, simplified validation, and more efficient use of plant floor space. Disposable bags greatly reduce the risk of cross contamination.

The stirred bag, single use bioreactor serves as typical stirred tank bioreactor and was first introduced in 2006 by Thermo Fisher Scientific. This bioreactor is equipped with an aeration device (sparger) and a mixing impeller assembly that ensures homogeneity of nutrients, pH, and temperature and gas dispersion inside the bag. The bag also includes gas inlet and exhaust filters and ports for integration of sensor probes for pH and DO control. The bag is generally shaped and fixed in a customized steel support container with a heating element (e.g., heating jacket).

Although the single use bioreactors offer advantages for shortening the time for the product development and launch to the market, the cell expansion in the upstream process in mammalian cell cultures still represents a challenge. The doubling time of mammalian cells is high compared to that of yeast or bacteria. This makes the upstream processing starting from a few milliliters seed vial until reaching the production scale too lengthy and effortful.

Traditional disposable bags bioreactors are designed as single compartment bags where cells are cultivated at a volume that should lie within a range of maximum and minimum working volumes predefined by the manufacturer for each bag. The ratio between the maximum and minimum working volume in most stirred tank traditional disposable bags bioreactors is from 1:2 to 1:5, and rarely reaches 1:10, so the maximum scale up of the cell culture in the same bag is ten times the initial volume at maximum while a traditional full production process requires usually thousands of volume multiplications.

This volume limitation for cell cultivation inside the disposable bags requires the use of several bags of different working volumes throughout the seed train process, which involves stepwise scale up of cell culture until inoculating the manufacturing scale bioreactor. The number of containers required in seed train is proportional to the final volume required to inoculate the manufacturing bioreactor and different volume disposable bioreactor bags usually requires different support structures in which the flexible bag is positioned. These supporting structures should have different dimensions that correspond with the dimensions of the bags. Also, the cultivation process inside different volume bags is controlled by different control units.

Thus, for a single process, multiple bags of different volumes, multiple support structures, and multiple control units are required. Besides the high dollar cost associated with multiple pieces of equipment, the equipment requires a large production area and a storage area where bags of different sizes are stored. Stepwise scale up process requires connecting separate bags every time for transferring cultivated cells and nutrient media from the smaller size to the larger size bag—a process that should be done under aseptic conditions and requires highly trained personnel.

SUMMARY OF THE INVENTION

According to an embodiment, a multi-chamber single-use bioreactor apparatus for cell culture expansion is disclosed. The bioreactor apparatus has bag assembly and a rigid support structure defining a bag receiving space. The bag assembly is disposed in the bag receiving space of the rigid support structure and supported by the rigid support structure. The bag assembly has at least a first bag and a second bag. The first bag defines a first reaction chamber, and the second bag defines a second reaction chamber. The first reaction chamber has a first volume, a first inlet, and a first outlet, and the second reaction chamber has a second volume different from the first volume, a second inlet, and a second outlet. The second inlet of the second bag is fluidically connected to the first outlet of the first bag so liquid in first reaction chamber can be transferred to the second reaction chamber. This embodiment greatly reduces the risk of contamination and the requirement of highly trained personnel. Also, in contrast to the traditional, single compartment, single use bioreactors, which require a seed train process for cell culture volume expansion starting from a few milliliters until transferring the cell culture to the final production bioreactor of hundreds or thousands of liters in volume, an embodiment of the inventive concepts eliminates the need for using multiple bioreactors before transferring the culture to the final bioreactor and allows much of the volume expansion process to occur in a single confined environment.

The bag assembly is supported by the support structure. Some bioreactor embodiments can accommodate cell cultivation at a volume range from 1 L or less to 1000 L, for example, or more in a closed system operated by a single control unit. This makes the bioreactor apparatus both cost and space efficient. It reduces risk of contamination, and it also reduces the production costs since only one disposable pre-sterilized bag is needed for the seed train process from 1 L-1000 L, for example, with only one control unit to operate. This reduces the factory footprint and the storage space. It also reduces the labor expenses since personnel interference in the process is minimized.

In one embodiment, the volume of the second reaction chamber is greater than the volume of the first reaction chamber, and the first bag is connected to the second bag. By way of example, the first bag can have a volume of 3.0 L and the second bag a volume of 50 L. In another embodiment, the first bag can have a volume of 10 L and the second bag a volume of 200 L. In yet another embodiment, the first bag can have a volume of 50 L and the second bag a volume of 1,000 L. And in yet another embodiment, the bag assembly can include a third bag fluidically connected to the second bag wherein the first bag can have a volume of 5 L, the second bag a volume of 100 L, and the third bag a volume of 1,000 L.

The first bag has a top end, a bottom end, and a sidewall. Similarly, the second bag has a top end, a bottom end, and a sidewall. The first bag is positioned on top of the second bag with the bottom end of the first bag connected to the top end of the second bag. The first bag and the second bag can be arranged concentrically with the top end of the second bag being depressed to form a pocket in which at least a portion of the first bag is disposed.

The bags are supported by a single supporting structure that corresponds to the dimensions of the largest bag and controlled by a single control unit. Also, all bags in the disposable bioreactor bag presented in an embodiment are interconnected through sterile and closed tubing systems that allow the cell culture transfer from one bag to another to be done using a pump (e.g., a peristaltic pump) without the need of opening the system. This decreases the risk of contamination by eliminating the processes of connecting separate bags for the transfer of the cell culture during the seed train process.

BRIEF DESCRIPTION OF THE DRAWINGS

FIG. 2 is a partially cross-sectional, elevational view of a mixing assembly.

FIG. 3 is a partially cross-sectional, elevational view of a bioreactor bag assembly showing a first bag connected to a second bag.

FIG. 4 is a partially cross-sectional, elevational view of the bioreactor bag assembly showing the first bag nested in the second bag.

DETAILED DESCRIPTION OF EXEMPLARY EMBODIMENTS

Figure 1:
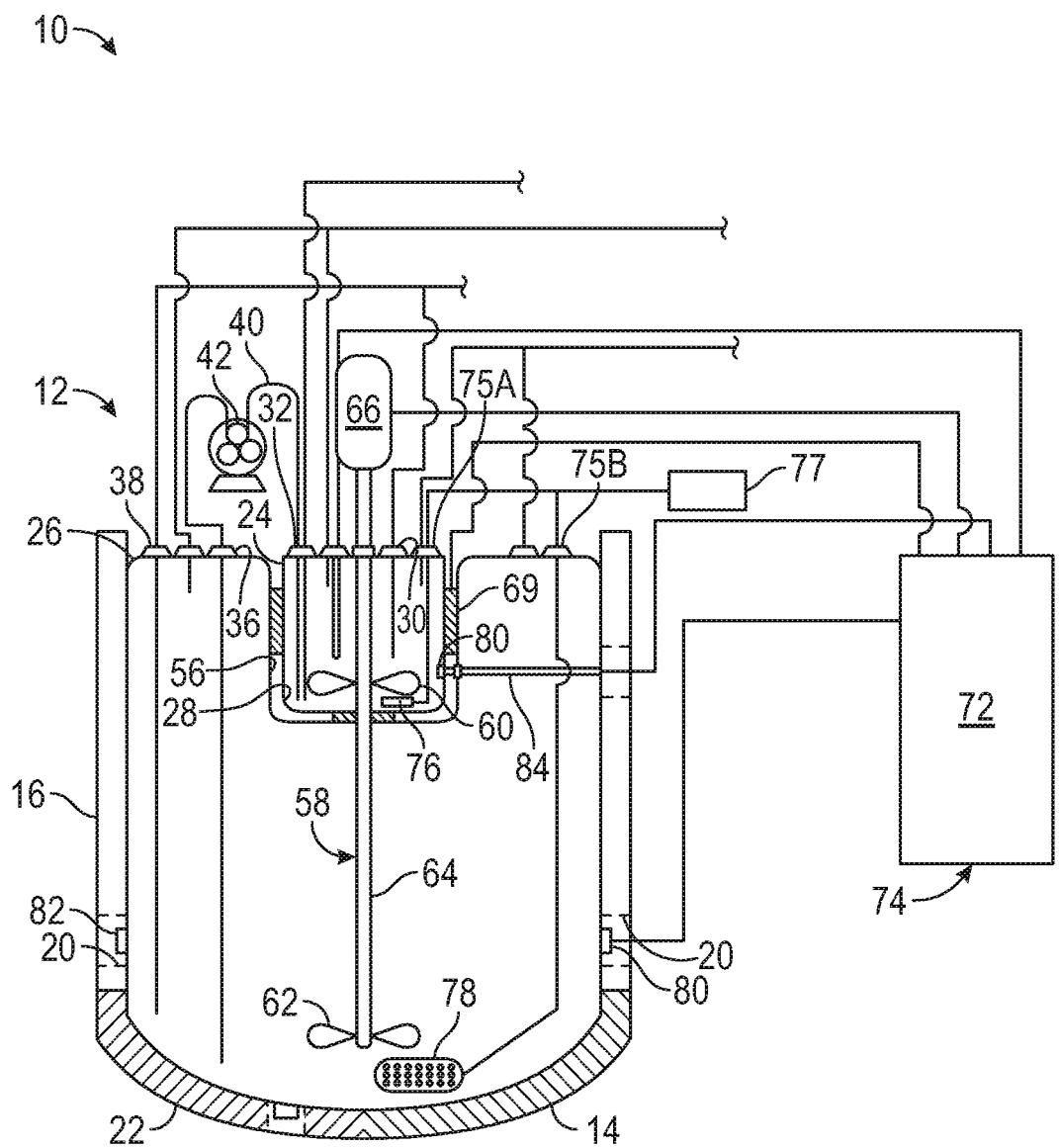
FIG. 1 is a schematic view of a multi-chamber bioreactor assembly constructed in accordance with the inventive concepts disclosed herein.

While this inventive concepts disclosed are susceptible of embodiment in different forms, there is shown in the drawings, and will be described, some specific embodiments of the inventive concepts. It should be understood, however, that the present disclosure is to be an exemplification of the principles of the invention and is not intended to limit the invention to the specific embodiments or algorithms so described.

It is to be understood that the terms "including," "comprising," "consisting," and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed there is only one of that element.

It is to be understood that where the specification states that a component, feature, structure, or characteristic "may," "might," "can," or "could" be included, that component, feature, structure, or characteristic need not be included.

Where applicable, although state diagrams, flow diagrams or both may describe embodiments, the invention is not limited to those diagrams or to the corresponding descriptions. For example, flow need not move through each illustrated box or state, or in the same order as illustrated and described.

Methods of the present invention may be implemented by performing or completing manually, automatically, or a combination thereof, selected steps or tasks.

The term "method" may refer to manners, means, techniques and procedures for accomplishing a task including, but not limited to, those manners, means, techniques and procedures either known to, or readily developed from known manners, means, techniques and procedures by practitioners of the art to which the invention belongs.

For this disclosure, the term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about," "substantially," "approximately,") should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)–(a second number)," this means a range whose lower limit is the first number and whose upper limit is the second number. For example, 25 to 100 should be interpreted to mean a range whose lower limit is 25 and whose upper limit is 100. And where a range is given, every possible subrange or interval within that range is also specifically intended unless the context indicates to the contrary. For example, if the specification indicates a range of 25 to 100 such range is also intended to include subranges, such as 26-100, 27-100, etc., 25-99, 25-98, and any other possible combination of lower and upper values within the stated range (e.g., 33-47, 60-97, 41-45, 28-96). Note that integer range values have been used in this paragraph for illustration only and decimal and fractional values (e.g., 46.7-91.3) should also be understood to be intended as possible subrange endpoints unless specifically excluded.

Where reference is made herein to a method comprising two or more defined steps, the defined steps can be carried out in any order or simultaneously (unless context excludes that possibility), and the method can also include one or more other steps carried out before the defined steps, between two of the defined steps, or after all of the defined steps (unless context excludes that possibility).

Further, terms of approximation (e.g., "about," "substantially," and "approximately") are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the inventive concepts may be in one or more appendices attached and/or filed, the disclosures of which are incorporated herein by reference as if set out.

A multi-chamber bioreactor apparatus for cell cultivation is disclosed. The bioreactor apparatus includes a flexible, disposable bag assembly supported by a support structure. The bag assembly has at least a first bag defining a first bioreactor chamber and a second bag defining a second bioreactor chamber. The second reaction chamber has a volume different from the volume of the first bag, and the second bag is fluidically connected to the first bag so liquid in first reaction chamber can be transferred to the second reaction chamber.

The second bag can be designed with any dimensions to accommodate and fit in any support structure. As a specific example, the first bag may have a volume of 3 L and the second bag may have a volume of 50 L. In another example, the first bag may have a volume of 3.0 L and the second bag a volume of 50 L. In yet another example, the first bag may have a volume of 10 L and the second bag a volume of 200 L. And in yet another example, the first bag may have a volume of 50 L and the second bag a volume of 1,000 L. And in yet another example, the bag assembly can include a third bag fluidically connected to the second bag wherein the first bag may have a volume of 5 L, the second bag a volume of 100 L, and the third bag a volume of 1,000 L. Thus, the bioreactor apparatus can accommodate cell cultivation at a volume range from 1 L to 1000 L in a closed system operated by a shared control unit.

The bioreactor apparatus can contain all fittings and accessories required for a typical cell cultivation process including gaseous exchange, mixing, pH, and dissolved oxygen sensors or probes, temperature sensors, and any other process control sensors/probes (e.g., metabolites, cell density, cell viability, foam detection).

The bioreactor apparatus, including all the fittings and accessories, is sterilized via gamma irradiation prior to use so after sterilization, the bag assembly, the support structure, and tubing are sterile and the bioreactor apparatus being isolated and protected from airborne contaminants can be safely used for cell cultivation.

The bags of the bag assembly may have a vertical and concentric arrangement with a common axis through the center. This common axis may have a common shaft for all bags where this shaft is part of bag assembly it will be in a direct contact with the fluid inside the bags. The common shaft is coupled to a motor from the top of the first bag. Impellers, which represent a part of the prior-to-use sterilized apparatus, are attached to the shaft where each bag has its own impeller with dimensions relevant to the bags working volume and dimensions.

Temperature control in the bags can be achieved by suitable heating elements, such as heating coils, heat blankets, and/or heat jackets. Filters for aeration and exhaust can be fitted where one filter for each aeration or exhaust purposes can have several branches from its outlet tube one for each bag in the invented system. Clamps at these branches can control the flow of air to/from the target bags.

Ports for insertion of probes/sensors are provided in the bags. Sensors and probes for monitoring pH and $pO_2$ levels in the culture can be designed in accordance to the control unit.

The multi-chamber bioreactor apparatus of this disclosure represents a system for housing and producing bio-chemicals (e.g., proteins, peptides, small molecules, etc.) for processing. Each reaction chamber can grow animal cells, plant cells, insect cells or microbial cultures. Each reaction chamber can also be used independently for sterile mixing and non-sterile mixing applications. The apparatus can also transfer or exchange fluids between different chambers through internal or external connections, without needing to open the system.

Various embodiments of the multi-chamber bioreactor might consist of two, three or even more chambers. In various embodiments the chambers will be connected together to form a continuous, single unit system where the processed material can be transferred from one chamber to another in a closed unit without the need to open the system. Chambers can be arranged so the larger chamber encloses the smaller one (e.g., nested within each other). The bags can be arranged in series with a single support structure so every chamber stands alone and is connected to the other chambers via tubing connections.

Referring now to the drawings, and particularly FIG. 1, shown is a multi-chamber bioreactor apparatus 10 constructed in accordance with the inventive concepts disclosed. The multi-chamber bioreactor 10 includes a disposable bag assembly 12 and a support structure 14 for supporting the bag assembly 12.

The support structure 14 can include a tank 16 (e.g., open topped, stainless steel) defining a bag receiving space 18. The tank 16 may include hooks (not shown) or other suitable structure from which the bag assembly 12 is suspended. The tank 16 may be supported by a plurality of legs (not shown). The tank 16 may include a height and diameter similar to standard stainless steel bioreactors. The design may be scaleable down to small bench bioreactor volumes and up over 1000 L working volumes, for example. Baffles (not shown) may be formed on the interior of the tank 16 to improve mixing by causing the bag assembly 12 to conform a shape that protrudes into the bag assembly. The tank 16 may include a sight window (not shown), which allows an observer to view a fluid level within the bag assembly 12. The tank 16 may include openings 20 through which tubing and sensor/probe ports may pass.

The tank 16 includes a heating element 22 to control the temperature of the contents of the bag assembly 12. The heating element 22 may be any suitable heating device, such as water jacket or heating blanket.

The bag assembly 12 includes at least a first bag 24 and a second bag 26. The first bag 24 and the second bag 26 may be fabricated of suitable flexible, polymeric materials, such as polyethylene (PE)-ethylene vinyl alcohol (EVOH) 9101 barrier film. The first bag 24 and the second bag 26 may be fabricated to be double layered with an inner layer made of PE and the outer layer made of PE/EVOH/nylon/PE.

The first bag 24 defines a first reaction chamber 28. The first reaction chamber 28 has a first volume, an inlet 30, and an outlet 32. The second bag 26 defines a second reaction chamber 34. The second reaction chamber 34 has a volume different from the volume of the first bag 24, an inlet 36, and an outlet 38. The inlet 36 of the second bag 26 is fluidically connected to the outlet 32 of the first bag 24 with a tubing 40 so liquid in first reaction chamber 28 can be transferred to the second reaction chamber 34. A pump 42, such as a peristaltic pump, is interposed in the tubing 40 for affecting the transfer of liquid.

Referring now to FIGS. 1-4, in one embodiment, the volume of the second reaction chamber 34 is greater than the volume of the first reaction chamber 28, and the first bag 24 is connected to the second bag 26. The first bag 24 has a top end 44, a bottom end 46, and a sidewall 48. Similarly, the second bag 26 has a top end 50, a bottom end 52, and a sidewall 54. The first bag 24 is positioned on top of the second bag 26 with the bottom end 46 of the first bag 24 connected to the top end 50 of the second bag 26. In one embodiment, the first bag 24 and the second bag 26 are arranged concentrically with the top end 50 of the second bag 26 being depressed to form a pocket 56 in which at least a portion of the first bag 24 is disposed. The first bag 24 can be connected directly to the second bag 26 by banding or heat welding or indirectly with connectors as described below.

The bag assembly 12 has a mixing assembly 58 for mixing liquid in the first reaction chamber 28 and liquid in the second reaction chamber 34. The mixing assembly 58 can include a first impeller 60 positioned in the first reaction chamber 28 and a second impeller 62 positioned in the second reaction chamber 34. Impellers for mixing the contents of bioreactors are well known. Therefore, no further description of the impellers is believed necessary. The mixing assembly 58 further includes a shaft 64 extending through the first reaction chamber 28 and into the second reaction chamber 34. The first impeller 60 and the second impeller 62 are connected to the shaft 64 so rotation of the shaft 64 causes the first impeller 60 and the second impeller 62 to rotate. The shaft 64 is operably connected to a motor 66.

In one embodiment, the shaft 64 is provided with two bearings 68a and 68b that rotatably support the shaft 64 and seal the first chamber 28 and the second chamber 34. The bearings 68a and 68b may be polyethylene housing disks. The bearing 68a is positioned on the top end 44 of the first bag 24 and the bearing 68b is positioned between the bottom end 46 of the first bag 24 and the top end 50 of the second bag 26. Each of bearings 68a and 68b contains an air/liquid tight seal to ensure aseptic conditions and to prevent culture leakage from the first bag 24 to the second bag 26. To construct the bag assembly 12, the top end 44 of the first bag 24 can be heat welded to a bottom surface of the bearing 68a. The bottom end 46 of the first bag 24 can be heat welded to an upper surface of the bearing 68b, and the top end 50 of the second bag 26 can be heat welded to a bottom surface of the bearing 68b to create the configuration of the first bag 24 on top of the second bag 26. As shown in FIG. 4, the first bag 24 may then be pressed or nested partially or fully into the second bag 26 to create a pocket 56.

To control the temperature of the contents of the first bag 24, the first bag 24 is provided with a heating element 69. In one embodiment, the heating element 69 may be a heating blanket fashioned about the first bag 24 so the heat blanket is positioned in the pocket 56 (FIG. 1). A thermocouple 70 is provided for sensing the temperature of the contents of the first bag 24, working with a control unit 72 to control a set temperature of the contents of the first bag 24.

The bag assembly 12 includes a control assembly 74 having an array of sensors and/or probes connected to the control unit 72, which is provided with suitable processing software.

Ports 75a and 75b are provided in the first bag 24 and the second bag 26, respectively, for receiving a supply of air or oxygen 77 to provide sparging to the contents of the first reaction chamber 28 and the second reaction chamber 34. The first bag 24 is provided with a sparge element 76, and the second bag 26 is provided with a sparge element 78. The sparge elements 76 and 78 may allow a gaseous sparge or fluids in and out of the first bag 24 and the second bag 26. Such sparging and/or fluid addition or removal may be used with the mixing assembly 58 (i.e., rotation of the impellers). Sparging provides air and oxygen necessary for cell growth and division, and carbon dioxide to control pH.

Sensors/probes and controls for monitoring and controlling process parameters include any one or more, and combinations of pH and dissolved oxygen (DO), for example. Ports 80a and 80b with integrated DO and pH sensors can be secured to the exterior surface of the first bag 24 and the second bag 26, and a sampling port and thermocouple port 82 can be provided on the exterior of the second bag 26. The port 80a of the first bag 24 is made accessible by forming a passage 84 through the second bag 26 with a tube. This passage acts as a channel to connect optical fibers between the control unit 72 and the sensors of the first bag 26, while maintaining the sterile conditions of both the first reaction chamber 28 and the second reaction chamber 34. Other ports for overlay gassing, exhaust and fluid sampling can be provided at the top ends of the first bag 24 and the second bag 26.

It will be appreciated that the volume of the first reaction chamber 28 and the second reaction chamber 34 can be varied. By way of example, the first bag 24 can have a volume of 3 L and the second bag 26 a volume of 50 L. The second bag 26 may have a minimum working volume of 12.5 L and a maximum of 50 L. The second reaction chamber 34 may have a diameter of 38.0 cm and an overall height of 67.0 cm. The liquid height at the maximum working volume is 44.0 cm; the aspect ratio of the fluid inside the chamber is 1.2, which lies within the 1-3 recommended range for stirred tank reactors.

In another embodiment, the first bag 24 can have a volume of 10 L and the second bag 26 a volume of 200 L. In yet another embodiment, the first bag 24 can have a volume of 50 L and the second bag 26 a volume of 1,000 L. And in yet another embodiment, the bag assembly can include a third bag (not shown) fluidically connected to the second bag wherein the first bag can have a volume of 5 L, the second bag a volume of 100 L, and the third bag a volume of 1,000 L.

The approach to mixing in the second bag 26 can be identical to that in the first bag 24. In one embodiment, the impellers 60 and 62 are top mounted, centered, 3-blade marine impellers. While one or both of the reaction chambers 28 and 34 can be baffled, both reaction chambers 28 and 34 are shown to be unbaffled. The ratio of the impeller diameter to the vessel diameter (D/T ratio) can be 0.55 in the 3 L chamber and 0.59 in the 50 L chamber. The sparge element 78 can have a 3-cm long pipe sparge element with 10 μm holes mounted below the impeller 62 in the second bag 26. The sparge element 76 in the first bag 24 may be a microsparger with 15-30 μm pore size.

The inventive concepts disclosed and claimed herein are well adapted to carry out the objects and to attain the advantages mentioned, and those inherent in the invention. While exemplary embodiments of the inventive concepts have been described for this disclosure, it will be understood that numerous changes may be made which will readily suggest themselves to those skilled in the art and which are accomplished within the spirit of the inventive concepts disclosed and/or as defined in the appended claims.

What is claimed is:

1. A bioreactor bag assembly, comprising:
a first flexible bag defining a first reaction chamber, the first reaction chamber having a first volume, a first inlet, and a first outlet; and
a second flexible bag defining a second reaction chamber, the second reaction chamber having a second volume greater than the first volume, a second inlet, and a second outlet, the second inlet of the second bag being fluidically connected to the first outlet of the first bag so liquid in the first reaction chamber can be transferred to the second reaction chamber,
wherein the first bag has a top end, a bottom end, and a sidewall, wherein the second bag has a top end, a bottom end, and a sidewall, and wherein the first bag is positioned on top of the second bag with the bottom end of the first bag connected to the top end of the second bag,
wherein the top end of the second bag is depressed to form a pocket in which at least a portion of the first bag is disposed; and
means for mixing liquid in the first reaction chamber and liquid in the second reaction chamber,
wherein the means for mixing comprises a first impeller positioned in the first reaction chamber, a second impeller positioned in the second reaction chamber, and a shaft extending through the first reaction chamber and into the second reaction chamber, the first impeller and the second impeller connected to the shaft so rotation of the shaft causes the first impeller and the second impeller to rotate.

2. The bioreactor bag assembly of claim 1, wherein the sidewall of the first bag is surrounded by a heating element.

3. The bioreactor bag assembly of claim 2, wherein the first reaction chamber and the second reaction chamber can accommodate reactions at a volume range from about 1 L to about 1000 L.

4. The bioreactor bag assembly of claim 2, wherein the volume of the first bag is about 3 L, and wherein the volume of the second bag is about 50 L.

5. The bioreactor bag assembly of claim 2, wherein the volume of the first bag is about 10 L, and wherein the volume of the second bag is about 200 L.

6. The bioreactor bag assembly of claim 2, wherein the volume of the first bag is about 50 L, and wherein the volume of the second bag is about 1,000 L.

7. The bioreactor assembly of claim 1, wherein the second bag has a passage extending through the second bag from the sidewall to the pocket.

8. The bioreactor assembly of claim 7, wherein the passage is aligned with a sensor on the first bag.

* * * * *